United States Patent
Sathyanarayana

(10) Patent No.: US 7,024,025 B2
(45) Date of Patent: Apr. 4, 2006

(54) NONUNIFORM ROTATIONAL DISTORTION (NURD) REDUCTION

(75) Inventor: Shashidhar Sathyanarayana, Fremont, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 541 days.

(21) Appl. No.: 10/072,355

(22) Filed: Feb. 5, 2002

(65) Prior Publication Data
US 2003/0147551 A1  Aug. 7, 2003

(51) Int. Cl.
G06K 9/00 (2006.01)

(52) U.S. Cl. ............................ 382/128; 600/467

(58) Field of Classification Search ........... 382/128; 600/467
See application file for complete search history.

(56) References Cited

U.S. PATENT DOCUMENTS

| | | | |
|---|---|---|---|
| 5,485,846 A | 1/1996 | Verdonk et al. | |
| 5,799,655 A | 9/1998 | Jang et al. | |
| 5,989,191 A | * 11/1999 | Scampini | ............ 600/453 |
| 6,152,878 A | 11/2000 | Nachtomy et al. | |
| 6,267,727 B1 | 7/2001 | Teo | |
| 6,450,964 B1 | 9/2002 | Webler | |
| 2003/0039377 A1 | 2/2003 | Rhoads et al. | |

OTHER PUBLICATIONS

Wahle, A. et al., "Geometrically correct 3-D reconstruction of intravascular ultrasound images by fusion with biplane angiography-methods and validation" IEEE Transactions on Medical Imaging, Aug. 1999, IEEE, USA, vol. 18, no. 8, pp. 686-699.

* cited by examiner

Primary Examiner—Brian Werner
Assistant Examiner—Christopher Lavin
(74) Attorney, Agent, or Firm—Orrick Herrington & Sutcliffe LLP

(57) ABSTRACT

A new image processing method reduces Nonuniform Rotational Distortion (NURD) in a medical image acquired using a rotating transducer. The image comprises a plurality of image vectors having texture. In a preferred embodiment, the image processing technique computes an average frequency of the texture for each image vector and estimates an angle for each image vector based on the average frequency for the respective image vector. The image processing technique then corrects for NURD by remapping each image vector to the estimated angle for the respective image vector.

23 Claims, 2 Drawing Sheets

NONUNIFORM ROTATIONAL DISTORTION (NURD) REDUCTION

BACKGROUND OF THE INVENTION

1. Field of the Invention

The invention relates generally to medical imaging, and more particularly to reducing Nonuniform Rotational Distortion (NURD) in medical images.

2. Background

For purposes of diagnosis and treatment planning, imaging techniques such as ultrasound imaging are commonly used in medical procedures to obtain images of the inside of a patient's body. In intravascular ultrasound (IVUS) imaging, images revealing the internal anatomy of blood vessels are obtained by inserting a catheter with an ultrasound transducer mounted on or near its tip into the blood vessel. The ultrasound transducer is positioned in a region of the blood vessel to be imaged, where it emits pulses of ultrasound energy into the blood vessel and surrounding tissue. A portion of the ultrasound energy is reflected off of the blood vessel wall and surrounding tissue back to the transducer. The reflected ultrasound energy (echo) impinging on the transducer produces an electrical signal, which is used to form an image of the blood vessel.

To obtain a cross-sectional image or "slice" of the blood vessel, the transducer must interrogate the vessel in all directions. This can be accomplished by mechanically rotating the transducer during imaging. FIG. 1 is a representation of an axial view of a rotating transducer 10 mounted on the tip of a prior art catheter 20. The transducer 10 is coupled to a drive motor (not shown) via a drive cable 30 and rotates within a sheath 35 of the catheter 20. The blood vessel 40 being imaged typically includes a blood region 45 and wall structures (blood-wall interface) 50 and the surrounding tissue.

A cross-sectional image of the blood vessel is obtained by having the transducer 10 emit a plurality of ultrasound pulses, e.g., 256, at different angles as it is rotated over one revolution. FIG. 1 illustrates one exemplary ultrasound pulse 60 being emitted from the transducer 10. The echo pulse 65 for each emitted pulse 60 received by the transducer is used to compose one radial line or "image vector" in the image of the blood vessel. Ideally, the transducer 10 is rotated at a uniform angular velocity so that the image vectors are taken at evenly spaced angles within the blood vessel 40. An image processor (not shown) assembles the image vectors acquired during one revolution of the transducer 10 into a cross-sectional image of the blood vessel 40. The image processor assembles the image vectors based on the assumption that the image vectors were taken at evenly spaced angles within the blood vessel 40, which occurs when the transducer 10 is rotated at a uniform angular velocity.

Unfortunately, it is difficult to achieve and maintain a uniform angular velocity for the transducer 10. This is because the transducer 10 is mechanically coupled to a drive motor (not shown), which may be located one to two meters from the transducer, via the drive cable 30. The drive cable 30 must follow all the bends along the path of the blood vessel to reach the region of the blood vessel 40 being imaged. As a result, the drive cable 30 typically binds and/or whips around as it is rotated in the blood vessel 40. This causes the transducer 10 to rotate at a nonuniform angular velocity even though the motor rotates at a uniform angular velocity. This is a problem because the angles assumed by the image processor in assembling the image vectors into the cross-sectional image of the blood vessel 40 are different from the actual angles at which the image vectors were taken. This causes the cross-sectional image of the blood vessel to be distorted in the azimuthal direction. The resulting distortion is referred as Nonuniform Rotational Distortion (NURD).

Therefore, there is need for an image processing technique that reduces NURD in IVUS images acquired using a rotating transducer

BRIEF DESCRIPTION OF THE DRAWINGS

The components in the figures are not necessarily to scale, emphasis instead being placed upon illustrating the concepts being discussed. All illustrations are intended to convey concepts, where relative sizes, shapes and other detailed attributes may be illustrated schematically rather than literally or precisely.

DETAILED DESCRIPTION OF THE PREFERRED EMBODIMENTS

Described below is a new image processing method that reduces NURD in IVUS images acquired using a rotating transducer. In an IVUS image of a blood vessel, the blood inside the blood vessel and the tissue surrounding the blood vessel have texture, which appear as speckles in the IVUS image. The blood typically has a fine image texture and the surrounding tissue has a course image texture. For an IVUS image taken with a transducer rotating at a uniform angular velocity, the image texture of the blood and the surrounding tissue should be fairly consistent throughout the image. However, when the transducer rotates at a nonuniform angular velocity, the image texture in the blood and the surrounding tissue becomes nonuniform. In regions of the image where the angular velocity of the transducer speeds up, the image texture becomes compressed in the azimuthal direction. In regions of the image where the angular velocity of the transducer slows down, the image texture becomes expanded, e.g., smeared out, in the azimuthal direction.

Therefore, the degree of texture compression/expansion in the image yields information about the relative angular velocity of the transducer during imaging. Using this principle, the new imaging processing method corrects for NURD in an image, as explained further below.

Figure 1:
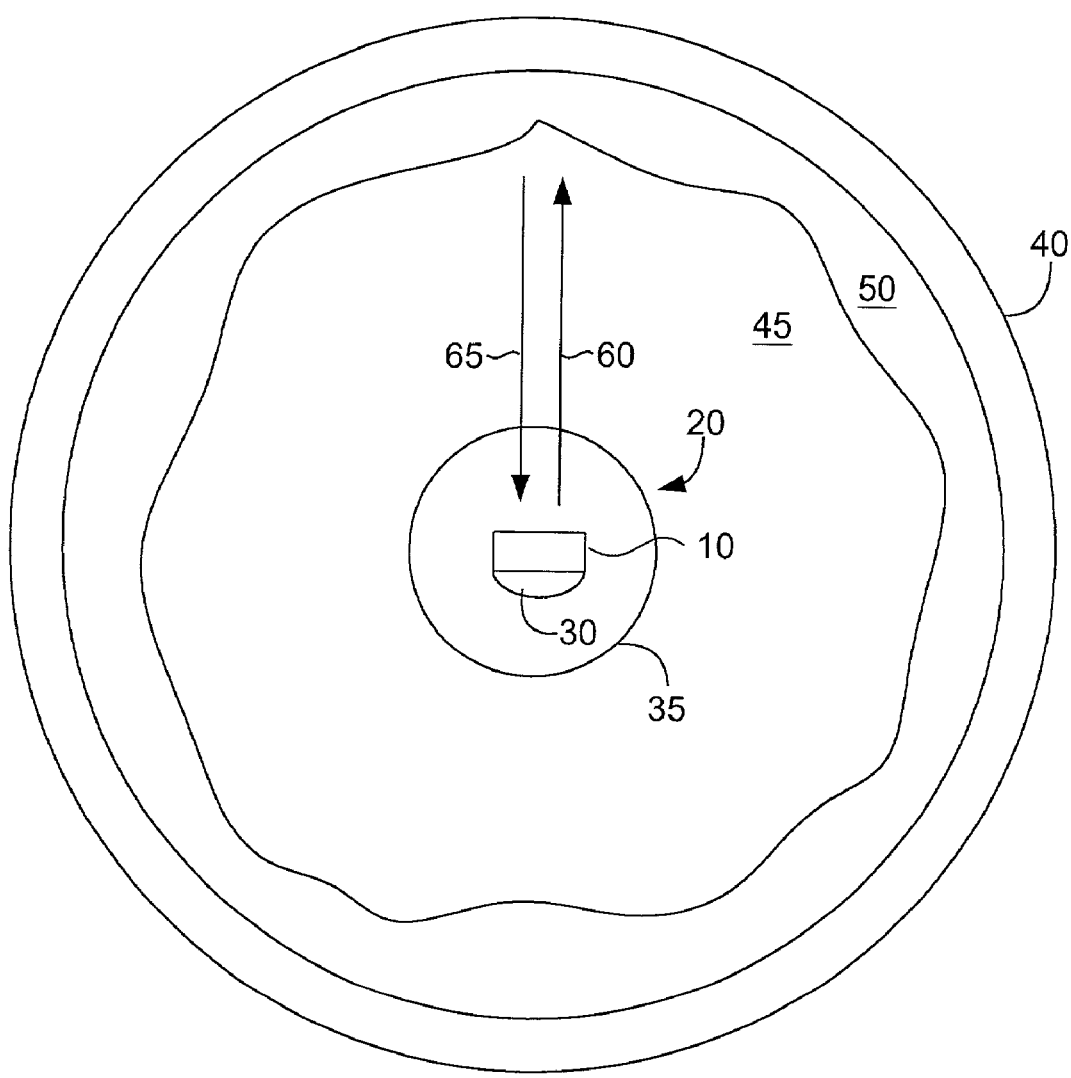
FIG. 1 is a representation of a rotating transducer of a prior art catheter inside a blood vessel.
Figure 2:
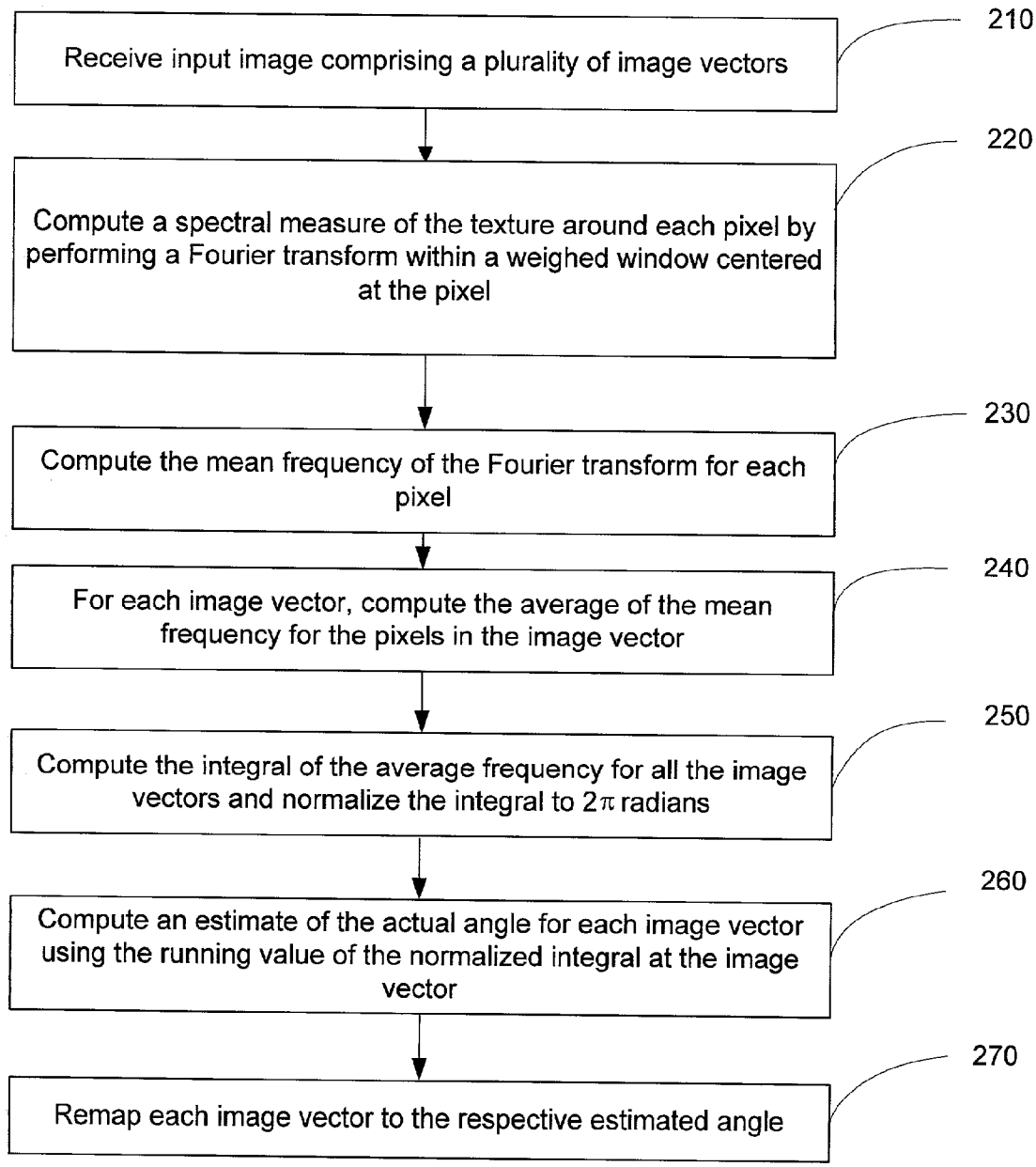
FIG. 2 is a flowchart illustration of an example embodiment of a new image processing method for reducing NURD in IVUS images acquired using a rotating transducer.

Turning now to FIG. 2, an example embodiment of a new image processing method for reducing NURD will be described. In step 210, an image processor receives an input image comprising a plurality of image vectors, e.g., 256 vectors. The image vectors are mapped onto angles in the image based on the assumption that the image vectors were taken at uniformly spaced angles. Each of the image vectors further comprises a plurality of pixels. The value of each pixel corresponds to the amplitude of a received echo pulse that is reflected back to the transducer from a certain angle and radial distance with respect to the transducer. The values of the pixels may be scaled according to a gray scale and/or a color scale.

In step 220, a spectral measure of texture around each pixel is computed in the azimuthal direction. This may be accomplished by performing a one-dimensional Fourier transform on a set of pixels within a weighted window centered at the pixel. The Fourier transform may be performed using standard signal processing techniques known to those of ordinary skill in the art. The Fourier transform for each pixel produces a frequency spectrum that contains local textural information for the pixel.

The weight of the window used in the Fourier transform may be computed using the following equation:

$$Weight = e^{-\left(\frac{n-\left(\frac{w+1}{2}\right)}{\chi}\right)^2}$$

where w is the width of the window, $\chi$ determines the drop off rate of the weight from the center of the window, and n is incremented from 1 to w. As an example, the width w may be 16 pixels and $\chi$ may be 4.

In step 230, the mean frequency of the Fourier transform for each pixel is computed. The mean frequency for each pixel provides a textural measure for the pixel with higher values indicating textural compression and lower values indicating textural blurring.

In step 240, for each image vector, the average value of the mean frequency for the pixels in the image vector is computed. The average frequency value for each image vector correlates with the relative angular velocity for the transducer at the image vector. A high average frequency value indicates a relatively high angular velocity for the transducer at the image vector and a low average frequency value indicates a relatively low angular velocity for the transducer at the image vector. For a transducer rotating at a constant angular velocity, the average frequency values for the image vectors is noted to be fairly constant.

In step 250, the integral of the average frequency values for all the image vectors is computed with the integral normalized to a value of 2 $\pi$ radians, which is the angle of one revolution of the transducer. In step 260, an estimate of the actual angle for each image vector is computed using the running value of the normalized integral at the image vector. This estimated angle for each image vector takes into account the fact that image vectors are not taken at uniformly spaced angles. In step 270, each image vector is remapped to its respective estimated angle to produce a NURD corrected image. In other words, NURD is reduced or eliminated by deriving an estimated angle for each image vector and using that estimated angle instead of the inaccurately assumed uniformly spaced angle.

The value of the width w and $\chi$ used to compute weight of the window in step 220 may be optimized through normal experimentation. For example, a phantom, e.g., made of rubber, having a known cross-sectional profile may be imaged using a rotating transducer. The NURD algorithm may then be applied to the image of the phantom while adjusting the values of w and $\chi$ until the NURD corrected image exhibits the least amount of NURD.

In the foregoing specification, the invention has been described with reference to a specific embodiment thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions, or As another example, features known to those of skill in the art can be added to the embodiment. Other processing steps known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A method for reducing Nonuniform Rotational Distortion (NURD) in an image, said image comprising a plurality of image vectors, each image vector having texture and each image vector being mapped to an angle in the image, the method comprising:
    computing an average frequency of the texture in the azimuthal direction for each image vector;
    estimating an angle for each image vector based on the average frequency for the respective image vector; and
    remapping each image vector to the estimated angle for the respective image vector.

2. The method of claim 1, wherein each image vector comprises a plurality of pixels, each pixel representing the amplitude of an echo pulse reflected from a certain image depth.

3. The method of claim 2, wherein the step of computing the average frequency for each image vector further comprises:
    computing a mean frequency of the texture for each pixel in each image vector; and
    computing an average of the mean frequency for the pixels in each image vector.

4. The method of claim 3, wherein the step of computing the mean frequency for each pixel further comprises:
    performing a Fourier transform around each pixel; and
    computing a mean of the Fourier transform for each pixel.

5. The method of claim 3, wherein the step of estimating the angle for each image vector further comprises:
    computing an integral of the average frequency for all of the image vectors;
    normalizing the integral to a predetermined value; and
    estimating the angle for the each image vector based on the value of the normalized integral at the respective image vector.

6. The method of claim 5, wherein the predetermined value is 2 $\pi$ radians.

7. The method of claim 1, wherein the step of estimating the angle for each image vector further comprises:
    computing an integral of the average frequency for all of the image vectors;
    normalizing the integral to a predetermined value; and
    estimating the angle for the each image vector based on the value of the normalized integral at the respective image vector.

8. The method of claim 7, wherein the predetermined value is 2 $\pi$ radians.

9. A computer program product that includes a medium useable by a processor, the medium comprising a sequence of instructions which, when executed by the processor, causes the processor to execute a method for reducing Nonuniform Rotational Distortion (NURD) in an image, the computer program product comprising:
    an instruction for receiving an input image, the input image comprising a plurality of image vectors, each image vector having texture and each image vector being mapped to an angle in the image;
    an instruction for computing an average frequency of the texture in the azimuthal direction for each image vector in the input image;

an instruction for estimating an angle for each image vector based on the average frequency for the respective image vector; and an instruction for producing an output image by remapping each image vector to the estimated angle for the respective image vector.

10. The computer program product of claim 9, wherein each image vector comprises a plurality of pixels, each pixel representing the amplitude of an echo pulse reflected from a certain image depth.

11. The computer program product of claim 10, wherein the instruction for computing the average frequency for each image vector further comprises:

an instruction for computing a mean frequency of the texture for each pixel in each image vector; and an instruction for computing an average of the mean frequency for the pixels in each image vector.

12. The computer program product of claim 11, wherein the instruction computing the mean frequency for each pixel further comprises:

an instruction for performing a Fourier transform on the image around each pixel; and an instruction for computing a mean of the Fourier transform for each pixel.

13. The computer program product of claim 9, wherein the instruction for estimating the angle for each image vector further comprises:

an instruction for computing an integral of the average frequency for all of the image vectors;

an instruction for normalizing the integral to a predetermined value; and an instruction for estimating the angle for the each image vector based on the value of the normalized integral at the respective image vector.

14. The computer program product of claim 13, wherein the predetermined value is 2 $\pi$ radians.

15. A medical imaging system comprising:
(a) a processor;
(b) an interface to receive data for the processor to use to create a medical image; and
(c) a medium useable by the processor, the medium comprising a sequence of instructions which, when executed by the processor, causes the processor to create a medical image with reduced Nonuniform Rotational Distortion (NURD), the medium including
(i) an instruction for receiving an input image, the input image comprising a plurality of image vectors, each image vector having texture and each image vector being mapped to an angle in the image;
(ii) an instruction for computing an average frequency of the texture in the azimuthal direction for each image vector in the input image;

(iii) an instruction for estimating an angle for each image vector based on the average frequency for the respective image vector; and (iv) an instruction for producing an output image by remapping each image vector to the estimated angle for the respective image vector.

16. The medical imaging system of claim 15 further comprising a display to display the output image.

17. The medical imaging system of claim 15 further comprising a printer to print the output image.

18. The medical imaging system of claim 15 further comprising:

a catheter; and an ultrasound transducer mounted on the catheter, the ultrasound transducer to be rotated by a motor, the ultrasound transducer to emit ultrasound waves and to receive reflected ultrasound waves, the ultrasound transducer to send reflected ultrasound waves to the interface.

19. The medical imaging system of claim 15, wherein each image vector comprises a plurality of pixels, each pixel representing the amplitude of an echo pulse reflected from a certain image depth.

20. The medical imaging system of claim 19, wherein the instruction for computing the average frequency for each image vector further comprises:

an instruction for computing a mean frequency of the texture for each pixel in each image vector; and an instruction for computing an average of the mean frequency for the pixels in each image vector.

21. The medical imaging system of claim 20, wherein the instruction for computing the mean frequency for each pixel further comprises:

an instruction for performing a Fourier transform on the image around each pixel; and an instruction for computing a mean of the Fourier transform for each pixel.

22. The medical imaging system of claim 15, wherein the instruction for estimating the angle for each image vector further comprises:

an instruction for computing an integral of the average frequency for all of the image vectors;

an instruction for normalizing the integral to a predetermined value; and an instruction for estimating the angle for the each image vector based on the value of the normalized integral at the respective image vector.

23. The medical imaging system of claim 22, wherein the predetermined value is 2 $\pi$ radians.

* * * * *